United States Patent
Nikolic et al.

(10) Patent No.: US 12,339,151 B2
(45) Date of Patent: Jun. 24, 2025

(54) FLOW SENSOR AND METHOD OF MEASURING A FLOW

(71) Applicant: FRESENIUS MEDICAL CARE DEUTSCHLAND GMBH, Bad Homburg (DE)

(72) Inventors: Dejan Nikolic, Bad Soden (DE); Alexander Heide, Eppstein (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 252 days.

(21) Appl. No.: 17/795,909

(22) PCT Filed: Jan. 28, 2021

(86) PCT No.: PCT/EP2021/052027
§ 371 (c)(1),
(2) Date: Jul. 28, 2022

(87) PCT Pub. No.: WO2021/152039
PCT Pub. Date: Aug. 5, 2021

(65) Prior Publication Data
US 2023/0084231 A1    Mar. 16, 2023

(30) Foreign Application Priority Data
Jan. 31, 2020   (DE) ............... 10 2020 102 485.1

(51) Int. Cl.
*G01F 15/02*    (2006.01)
*A61M 1/16*    (2006.01)
(Continued)

(52) U.S. Cl.
CPC ......... *G01F 15/02* (2013.01); *A61M 1/36224* (2022.05); *G01F 1/588* (2013.01);
(Continued)

(58) Field of Classification Search
CPC .... G01F 15/02; G01F 1/588; A61M 1/36224; A61M 1/3663; A61M 1/3669;
(Continued)

(56) References Cited

U.S. PATENT DOCUMENTS

2012/0279910 A1* 11/2012 Wallace ............... A61M 1/154
                                                      137/511
2015/0135848 A1   5/2015 Suzuki
(Continued)

FOREIGN PATENT DOCUMENTS

DE          1 573 007       6/1970
DE  10 2010 001 993 A1      8/2011
(Continued)

*Primary Examiner* — Peter J Macchiarolo
*Assistant Examiner* — John M Royston
(74) *Attorney, Agent, or Firm* — Kilyk & Bowersox, P.L.L.C.

(57) ABSTRACT

The present invention relates to a flow sensor for measuring a flow difference having at least two measurement chambers through which fluid is conductible; at least one means for producing a magnetic field for charge separation in a fluid flowing through the at least two measurement chambers; and at least one means for measuring an electric potential in the fluid flowing through the at least two measurement chambers, with the at least two measurement chambers being arranged such that they are run through by the same magnetic field line of the magnetic field for charge separation.

11 Claims, 4 Drawing Sheets

(51) Int. Cl.
*A61M 1/36* (2006.01)
*G01F 1/58* (2006.01)

(52) U.S. Cl.
CPC ......... *A61M 1/1607* (2014.02); *A61M 1/1609* (2014.02); *A61M 1/3663* (2013.01); *A61M 1/3669* (2013.01); *A61M 2205/3317* (2013.01); *A61M 2205/3334* (2013.01); *A61M 2205/3372* (2013.01)

(58) Field of Classification Search
CPC .. A61M 2205/3317; A61M 2205/3334; A61M 2205/3372; A61M 1/1607; A61M 1/1609
USPC ...................................................... 73/861.11
See application file for complete search history.

(56) References Cited

U.S. PATENT DOCUMENTS

2016/0341366 A1   11/2016  Nikolic et al.
2018/0031399 A1    2/2018  Heide et al.

FOREIGN PATENT DOCUMENTS

| DE | 10 2010 003 642 A1 | 9/2011 |
|---|---|---|
| EP | 3 254 066 B3 | 12/2017 |
| GB | 2003 274 A | 3/1979 |
| JP | 5467576 | 4/2014 |
| WO | WO 2011/113838 | 9/2011 |
| WO | WO 2015/197424 A1 | 12/2015 |
| WO | WO 2019/139671 A1 | 7/2019 |

\* cited by examiner

FLOW SENSOR AND METHOD OF MEASURING A FLOW

The present invention relates to a flow sensor for measuring a flow difference and to a method of measuring a flow difference.

The present invention in particular relates to a magnetically inductive sensor for measuring the difference of a flow of fluid flows that flow through two measurement chambers or channels.

The flow difference (inlet minus outlet) (also called a flow balance) of fluids or liquids is an important parameter, for example, in dialysis treatments. It is important that the water balance of dialysis patients is not negatively influenced as part of a treatment, but rather that the achieving of a healthy water balance is assisted by the treatment. The liquid balance of a patient has to be known as exactly as possible for this purpose.

The flow difference can in principle be directly measured or can be determined by the offsetting of two absolute measurements of the flow. A direct differential flow measurement can be achieved more accurately (or less expensively) than an indirect difference measurement by a combination of two absolute measurements whose difference is calculated since absolute measurements are per se complex and/or expensive with respect to their measurement accuracy and are additionally more susceptible to error. A direct differential measurement in contrast can achieve a higher accuracy with a smaller effort because the measurement errors of the absolute measurement that occur (per channel) cancel one another out.

The measurement accuracy is nevertheless still a problem in known differential flow sensors such as in the flow sensor of the category known from JP5467576 (B2).

Starting from here, advantageous further developments were, for example, disclosed in WO 2015/197424 and in EP 3 254 066 B1, from which in each case disposable sensor cassettes having electrodes for arrangement in a magnet yoke are known.

The measurement principle respectively comprises providing two measurement channels that are each passed through by a magnetic field perpendicular to the direction of flow and have two or more electrodes (arranged perpendicular to the magnetic field and the direction of flow). Oppositely poled charge carriers are separated in the fluid by the magnetic field (Hall effect) and are transported perpendicular to the magnetic field vector and to the direction of flow.

In the case of the solutions disclosed in WO 2015/197424 and EP 3 254 066 B1, electrodes that are intended to measure the potential resulting from the charge separation are located at the two channel margins. The electric potential in the liquid resulting from the charge separation is measured by means of these measurement electrodes.

There is, however, the problem with these known sensors that a measurement accuracy sufficient for an extracorporeal blood treatment, in particular a dialysis, is not ensured over time.

This stems from the fact that over time even microscopic displacements or vibrations of the sensor cassette are sufficient to produce non-tolerable measurement errors. Since the magnetic field is not perfectly homogeneous in the known sensors, the two measurement chambers or channels are differently passed through by field lines of a magnetic field.

Temperature variations and vibrations are therefore already sufficient to lead the measurement accuracy out of the range tolerable for dialysis with the known sensors.

Vibrations occur, for example, due to pumps, e.g. roller pumps or membrane pumps, due to inherent vibration, or due to pressure impulses on the fluid flowing through the measurement channels. In the case of dialysis, the movement of the lines by a patient can moreover produce further displacements of the sensor and can thus further degrade the measurement accuracy.

It is the underlying object of the present invention to alleviate or even to fully eliminate the problems known from the prior art and in particular to provide an improved differential flow sensor that provides a sufficient measurement accuracy over a measurement time of a plurality of hours.

This object is achieved by a flow sensor and by a blood treatment device and a system in accordance with the independent claims. Further advantageous further developments of the invention are the subject of the dependent claims.

A flow sensor in accordance with the invention for measuring a flow difference comprises: at least two measurement chambers through which fluid is conductible; at least one means for producing a magnetic field for charge separation in a fluid flowing through the at least two measurement chambers; and at least one means for measuring an electric potential in the fluid flowing through the at least two measurement chambers, with the at least two measurement chambers being arranged such that they are run through by the same magnetic field line of the magnetic field for charge separation.

In other words, in accordance with the invention, the arrangement of the measurement chambers (or channels) in a flow sensor is such that the geometrical regions of both measurement channels in which the flows of the fluid are measured are arranged such that they are passed through by the same magnetic field lines.

The two measurement chambers or the regions of the measurement chambers are, for example, arranged above one another, below one another, or also next to one another. The arrangement is arbitrary as long as it is ensured that both measurement chambers or the regions of the measurement chambers in which the flows of the fluid are measured are run through by the same magnetic field lines.

A flow sensor having such an arrangement is robust toward temperature variations, vibrations, and further environmental influences because both measurement chambers or channels are always affected to the same degree by the environmental influences.

It results from this that the variations are negligible in a differential measurement since the same conditions with respect to the magnetic field are present in both measurement chambers or the magnetic field in both measurement chambers is influenced to the same degree by the environmental influences.

The means for measuring an electric potential preferably comprises one or more measurement electrodes. Each measurement chamber or each channel preferably has two measurement electrodes.

In other words, in accordance with a preferred embodiment, each of the two measurement chambers has a means for measuring an electric potential associated with it and the at least two measurement chambers and/or the means for measuring an electric potential associated with them are aligned with one another.

In a particularly preferred embodiment, the measurement electrodes of both channels are arranged flush or in alignment such that their projection onto a plane (extending in parallel with the flow of the fluid and perpendicular to the magnetic field) is exactly congruent.

The flow sensor or the cassette comprising it is thereby designed such that it can be placed in a magnet yoke, for example of a blood treatment device, such that the measurement regions in both channels are passed through by exactly the same field lines.

The manner in which the electric potential resulting from the magnetically induced charge separation is measured is arbitrary. Electrodes that are in direct contact with the fluid can, for example, be used or measurement can be made indirectly capacitively. The shape, number, and positioning of the measurement means, in particular of the measurement electrodes, is furthermore arbitrary. More than two electrodes can also be used.

An indirect measurement of the potential would equally be conceivable. The electrical field is, for example, measured capacitively here. In a capacitive measurement, the measurement means for measuring the electrical field are not located in the fluid, but are rather arranged outside it (separated by an isolator).

A flow sensor in accordance with the invention is preferably a magnetically inductive differential flow sensor.

It has proven advantageous in practice for the flow sensor to additionally have a temperature sensor for measuring the temperature of a fluid.

Two synergistic advantages result when a temperature is also measured in the flow sensor. First, as a rule, a temperature measurement of the fluids or liquids is necessary for the carrying out of an extracorporeal blood treatment. If the flow sensor also takes over the temperature measurement in an integrated manner, an additional sensor that would take up additional liquid volume, can advantageously be omitted.

Second, when the temperature is known, a correction of flow measurement values or of the measurement accuracy can be carried out.

A flow sensor that also serves as a temperature sensor is preferably used in interaction with an extracorporeal blood treatment device, in particular a dialysis machine.

In accordance with a preferred embodiment, a treatment machine into which the cassette having the flow sensor in accordance with the invention can be placed has an infrared diode and an evaluation device that evaluates the light measured by the diode and thus determines the temperature of a medium or fluid located before the diode. Corresponding to the diode, a cutout or a kind of "window" is provided in the cassette of the flow sensor.

The wall thickness in the window region preferably amounts to approximately 300 µm to approximately 600 µm, in particular to approximately 500 µm. Other thicknesses are conceivable. Alternatively, for example, a PT1000 sensor can be used for the temperature measurement.

The temperature sensor is preferably integrated and/or fixedly installed in a cassette having the flow sensor. In this case, an associated evaluation unit is preferably also integrated in the cassette. Alternatively or additionally, the temperature sensor and/or the evaluation device can also be provided on the side of the blood treatment device and can be associated with or connected to the cassette.

Alternatively or additionally, the flow sensor can have a conductivity sensor for measuring the conductivity of a fluid. The conductivity sensor is preferably also integrated and/or fixedly installed in a cassette having the flow sensor. In this case, an associated evaluation unit is preferably also integrated in the cassette.

Alternatively or additionally, the temperature sensor and/or the evaluation device can also be provided on the side of the blood treatment device and can be associated with or connected to the cassette.

A preferred embodiment for a measurement arrangement of the conductivity has three electrodes that are arranged behind one another in the direction of flow in the fluid channel (in contact with the fluid). In this respect, the middle electrode is preferably designed as an areal rectangle and the two other electrodes are each designed as a "U" engaging around the fluid channel. All three electrodes are preferably produced from stainless steel.

In measurement operation, a voltage is thus applied to the middle electrode so that a current flows through the fluid to the electrodes disposed downstream and upstream. The two outer electrodes are grounded. The voltage drop between the middle electrode and the outer electrodes is measured, as is the flowing current. The conductance is measured from the current and the voltage drop. When the geometry is known, the conductivity of the fluid can be determined therefrom.

The evaluation device that determines a conductivity from the measured electrical values at the electrodes is preferably a part of the treatment machine, not of the flow sensor cassette. The sensor cassette can thus be designed in a particularly inexpensive manner, which enables a design as a disposable article.

The flow sensor and/or the cassette having it can generally be designed as a disposable or as a multiple use article.

A further aspect of the present invention relates to a blood treatment device, in particular to a dialysis device, that is configured to be used with a flow sensor in accordance with the invention or that has a flow sensor in accordance with the invention.

It has proved advantageous in practice for the blood treatment device to be configured to at least partly releasably receive a flow sensor in accordance with the invention and preferably to be equipped with a mount for the flow sensor for this purpose.

The design of the mount is arbitrary. The mount of the blood treatment device can, for example, be designed as a pair of pincers (preferably with inwardly disposed electrical contacts) or as a recess such as a slit.

It is equally conceivable that the mount has the design of a recess that can be closed by means of a door when the sensor cassette has been placed into the recess. The door can be designed, e.g. preloaded, such that it holds the recess closed when a user does not actively open the door.

Latching elements can equally be provided that hold the sensor cassette at or in the blood treatment device.

It has furthermore proved advantageous for the at least one means for producing a magnetic field for charge separation to be arranged at the side of the blood treatment device in a fluid flowing through the at least two measurement chambers. In other words, one or more magnets are preferably provided at the blood treatment device.

The at least one means for producing a magnetic field for charge separation preferably comprises at least two magnetic poles that are arranged at mutually opposite sides of a mount for the flow sensor or for the sensor cassette. This embodiment is in particular advantageous when the flow sensor is designed as a disposable. Alternatively, two electromagnets can also be used.

A further aspect of the invention relates to the use of a flow sensor in accordance with the invention and/or of a blood treatment device in accordance with the invention for blood-blood balancing. Due to the compact construction of the flow sensor in accordance with the invention, only a little blood is required for the measurement so that the flow sensor in accordance with the invention is particularly suitable for such an application.

WO 2019/139671 A1, for example, discloses a treatment that comprises a "donation" of the dialysis capability of a healthy kidney of a first person to a second person with renal insufficiency. In this respect, a dialyzer can also be used. A balance sensor in accordance with the invention can be used versatilely to measure the change of the liquid balance (water balance) of the person with renal insufficiency.

For example, a flow sensor in accordance with the invention for detecting the fluid balance (inlet minus outlet) of the dialyzer can be used for the person with renal insufficiency. It is assumed in this respect that the healthy person can independently regulate his/her water balance.

Optionally, a second balance sensor could be used for reasons of completion that determines the fluid balance (inlet minus outlet) of the dialyzer for the healthy person.

Alternatively, two flow sensors in accordance with the invention can also be used for the blood-blood balancing. In this respect, a differential flow sensor in accordance with the invention is preferably respectively used at the inlet and at the outlet of the dialyzer. In this embodiment of a use of a flow sensor presented here, the liquid balance for the two dialyzer halves or for the two persons would therefore take place in a second step. In the first step, an "inlet balance" (inlet flow person 1 in the dialyzer is measured differentially with respect to the inlet flow of person 2 in the dialyzer) by a first sensor and an "outlet balance" is simultaneously measured at the outlet of the dialyzer. A fluid balance for both persons can be calculated from these two balances in a second step, for example in that the "outlet balance" is deducted from the "inlet balance".

The difference of the flow at the inlet of the dialyzer for the healthy person and for the person with renal insufficiency is determined by means of the flow sensor at the inlet of the dialyzer.

Analogously to this, the difference of the flow from the dialyzer for the healthy person and for the person with renal insufficiency is determined at the outlet of the dialyzer. A conclusion on the net water flow of both persons can be drawn from both differences.

A further aspect of the invention relates to a method of measuring a flow difference of a fluid, preferably using a flow sensor in accordance with the present invention, comprising the steps:

conducting fluid through at least two measurement chambers or channels;
producing a magnetic field for charge separation in the fluid; and
measuring an electric potential in the fluid flowing through the at least two measurement chambers, wherein
the magnetic field for charge separation is produced such that the same magnetic field line of the magnetic field for charge separation runs through the at least two measurement chambers.

The method preferably also comprises the upstream step of placing a flow sensor cassette into a corresponding mount of a blood treatment device in accordance with the invention.

In accordance with an advantageous embodiment, the method additionally comprises the step: detecting the temperature of the fluid, preferably by means of a temperature sensor integrated in the flow sensor.

Alternatively or additionally, the method additionally comprises the step:

detecting the conductivity of the fluid, preferably by means of a conductivity sensor integrated in the flow sensor.

Further advantages, feature, and effects of the present invention result from the following description of preferred embodiments with reference to the Figures. Components that are the same or similar are marked by the same reference numerals in the drawings. There are shown.

and

Figure 1:
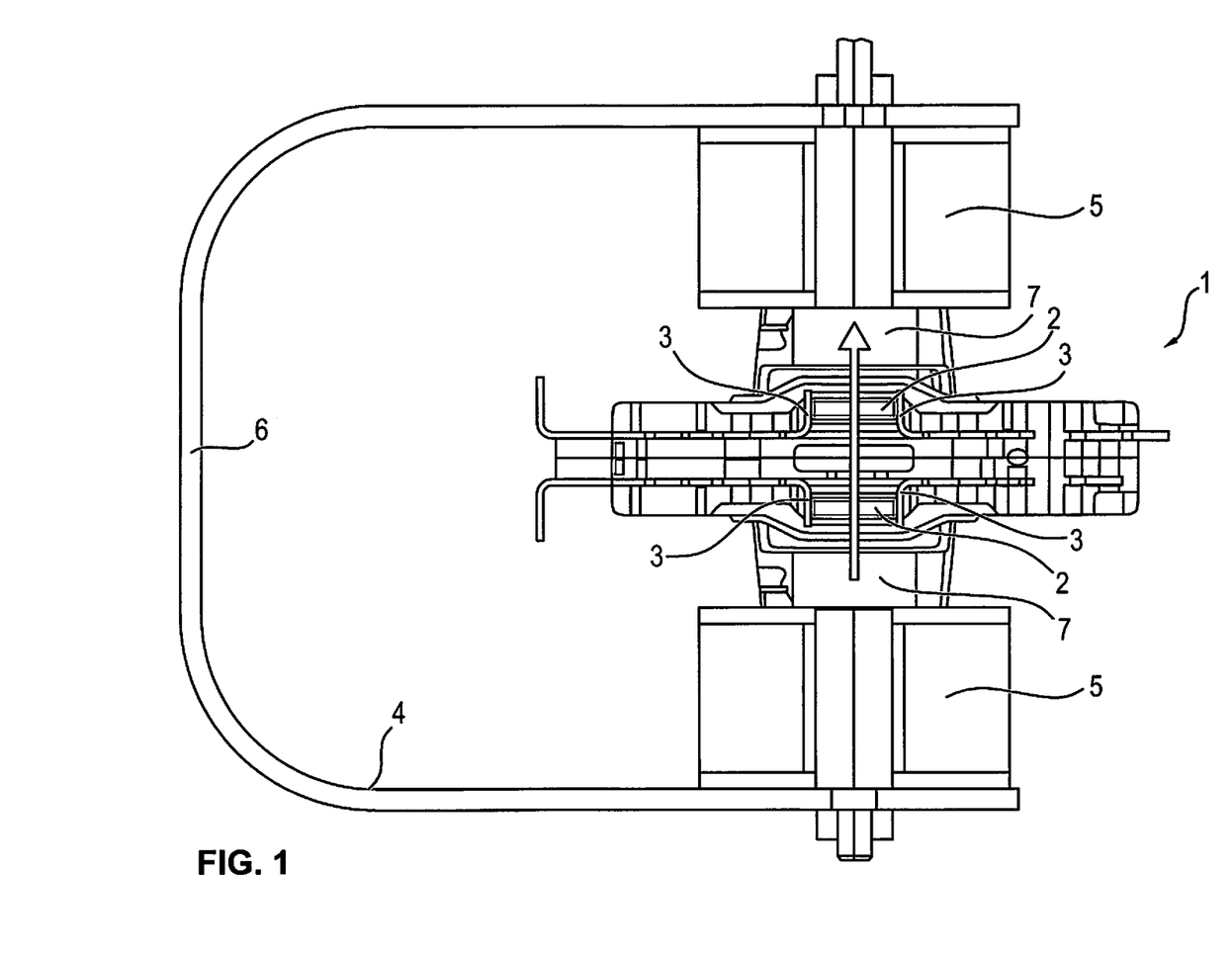
FIG. 1 a cross-section of a flow sensor in accordance with the invention.

As shown in FIG. 1, a flow sensor 1 in accordance with the invention has two measurement chambers or channels 2 that are flowed through by a fluid in the measurement. A respective measurement electrode 3 is arranged at mutually oppositely disposed sides of each measurement chamber 2 to measure an electric potential produced due to the charge separation in the fluid.

The sensor is inserted into a magnet yoke 4 that has two magnetic coils 5 that are connected to one another by means of a hoop 6. Magnetic poles 7 are arranged between the coils 5 and the measurement chambers 2. A magnetic field is produced by means of the magnets and its magnetic vector is reproduced by the perpendicular arrow shown in FIG. 1. The magnetic field vector runs orthogonally to the direction of flow of the fluid in the measurement chambers that runs orthogonally to the plane of the paper in FIG. 1.

Figure 2:
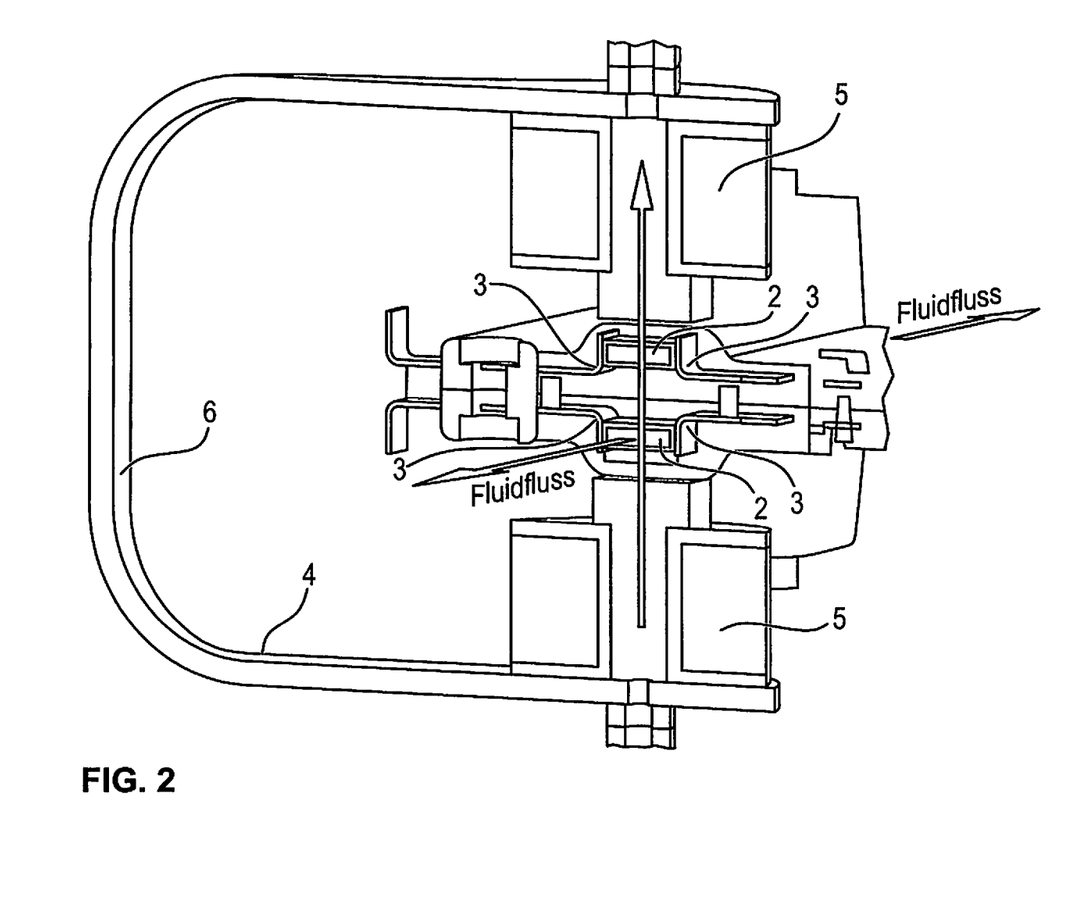
FIG. 2 a further cross-section of a flow sensor in accordance with the invention.

The direction of flow of the fluid is reproduced by two opposed arrows in FIG. 2. The magnetic field vector runs orthogonally to the direction of flow of the fluid.

Figure 3:
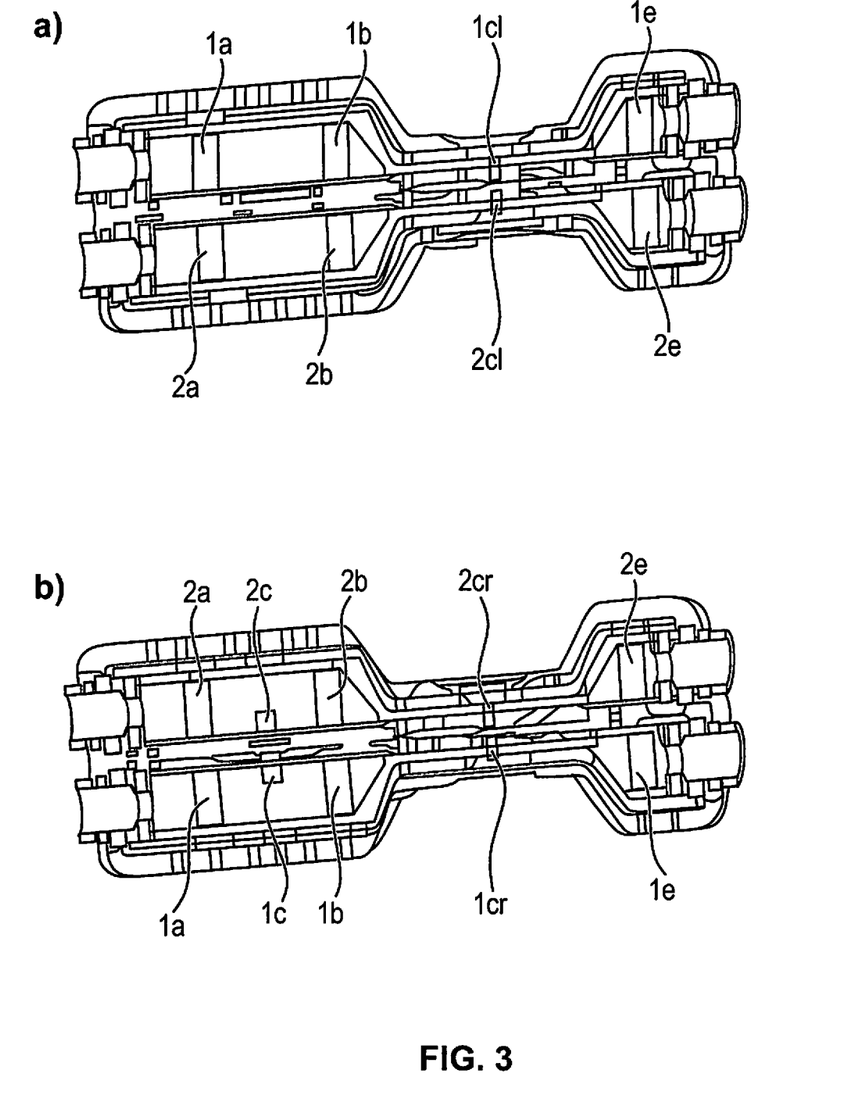
FIG. 3 a longitudinal section of a flow sensor in accordance with the invention.

FIG. 3 shows a longitudinal section of a flow sensor in accordance with the invention in FIGS. 3a) and 3b) respectively. The representation in FIG. 3b) is rotated with respect to the representation in FIG. 3a).

The flow sensor shown in FIG. 3 is not only adapted for a differential flow measurement, but also has an integrated temperature sensor and an integrated conductivity sensor.

As shown in FIGS. 3a and 3b, a flow sensor in accordance with this embodiment has three electrodes for the conductivity measurement. They are marked by the reference numerals $1a$, $1b$, $1c$ and $2a$, $2b$, $2c$. The electrode marked by reference numeral $1a$ or $2a$ serves as the ground as part of the conductivity measurement. The electrode marked by reference numeral $1c$ or $2c$ serves as the hot electrode as part of the conductivity measurement. The electrode marked by reference numerals $1b$ or $2b$ is likewise used as part of the conductivity measurement.

Electrodes $1cl$ and $1cr$ preferably serve as measurement electrodes of the flow measurement and are respectively arranged to the left ($1cl$) and to the right ($1cr$) of a measurement chamber. Electrodes $2cl$ and $2cr$ preferably serve as measurement electrodes of the flow measurement and are respectively arranged to the left ($2cl$) and to the right ($2cr$) of a measurement chamber.

Reference numerals $1cl$ and $2cl$ thus respectively mark the left measurement electrode and reference numerals $1cr$ and $2cr$ respectively mark the right measurement electrode.

Figure 4:
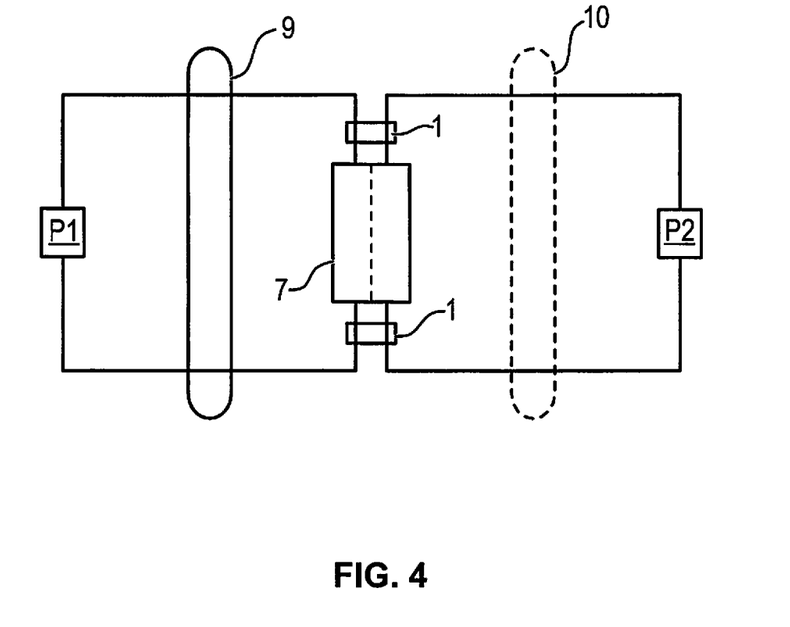
FIG. 4 a diagram illustrating the use of a sensor in accordance with the invention for blood-blood balancing.

FIG. 4 is a diagram illustrating the use of a sensor in accordance with the invention for blood-blood balancing.

In the setup shown in FIG. 1, the dialysis capability of a healthy kidney of a person P2 is provided to a person with renal insufficiency P1. A dialyzer 7 having a membrane 8 is used in this process.

A balance sensor in accordance with the invention can be used versatilely to measure the change of the liquid balance or water balance of the person with renal insufficiency P1.

A balance (inlet minus outlet of the dialyzer) for the person with renal insufficiency P1 is, for example, determined by means of a flow sensor 1 in accordance with the invention. This balance is indicated as an ellipse 9 in FIG. 4. It is assumed here that the healthy person P2 independently regulates his/her water balance. The balance (inlet minus outlet of the dialyzer) for the healthy person P2 is therefore shown as a dashed ellipse 10 in FIG. 4.

The balance for the healthy person can be determined by means of a second flow sensor 1 that balances inlet against outlet at the side of the dialyzer associated with the healthy person P2.

Two sensors 1 in accordance with the invention are shown in FIG. 4. This is, however, only an example and only one flow sensor 1 can also be provided that determines the fluid balance of person P1 or person P2.

The invention claimed is:

1. A flow sensor for measuring a flow difference comprising:
   at least two measurement chambers through which fluid is conductible;
   at least one means for producing a magnetic field for charge separation in a fluid flowing through the at least two measurement chambers, the magnetic field for charge separation having magnetic field lines;
   at least one means for measuring an electric potential in the fluid flowing through the at least two measurement chambers;
   a temperature sensor for measuring the temperature of a fluid flowing through the at least two measurement chambers, the temperature sensor being configured to detect the temperature of the fluid in the flow sensor; and
   an evaluation device, wherein
   the at least two measurement chambers are arranged such that they are run through by the same magnetic field lines of the magnetic field for charge separation, and
   the evaluation device is configured to determine respective flow measurement values of fluid flowing through the at least two measurement chambers, correct the respective flow measurement values based on the temperature of the fluid in the flow sensor, which is measured by the temperature sensor, and determine a differential flow measurement of the fluid flowing through the at least two measurement chambers by offsetting the corrected flow measurement values.

2. The flow sensor in accordance with claim 1, wherein the flow sensor is a magnetically inductive differential flow sensor.

3. The flow sensor in accordance with claim 1, wherein the flow sensor additionally has a conductivity sensor for measuring the conductivity of a fluid.

4. The flow sensor in accordance with claim 1, wherein the at least one means for measuring an electric potential comprises two means for measuring an electric potential, and each of the two measurement chambers has a respective one of the two means for measuring an electric potential, associated with it, and the at least two measurement chambers and/or the two means for measuring an electric potential are aligned with one another.

5. The flow sensor in accordance with claim 1, wherein the flow sensor, with the exception of the evaluation device, is designed as a disposable cassette.

6. A dialysis machine comprising the flow sensor in accordance with claim 5, wherein the evaluation device is part of the dialysis machine.

7. The dialysis machine in accordance with claim 6, wherein the dialysis machine is adapted to at least partly releasably receive the disposable cassette and is equipped with a mount for the disposable cassette configured for this purpose.

8. A system comprising a blood treatment device and a flow sensor in accordance with claim 1, wherein the at least one means for producing a magnetic field for charge separation is arranged at a side of the blood treatment device and in a fluid flowing through the at least two measurement chambers.

9. The system in accordance with claim 8, wherein the flow sensor, with the exception of the evaluation device, is designed as a disposable cassette, the blood treatment device comprises a mount for the disposable cassette, and the at least one means for producing a magnetic field for charge separation comprises at least two magnetic poles that are arranged at mutually opposite sides of the mount for the disposable cassette.

10. A method for determining a differential flow measurement of a fluid flowing through two measurement chambers, comprising the steps of:
    conducting fluid through a first measurement chamber and through a second measurement chamber of a flow sensor;
    producing a magnetic field for charge separation in the fluid in the first measurement chamber and in the second measurement chamber;
    measuring an electric potential in the fluid flowing through the first measurement chamber;
    measuring an electric potential in the fluid flowing through the second measurement chamber, wherein the magnetic field for charge separation is produced such that the same magnetic field lines of the magnetic field for charge separation run through both the first measurement chamber and the second measurement chamber;
    determining a first flow measurement value for the flow of fluid flowing through the first measurement chamber, based on the measured electrical potential of the fluid flowing through the first measurement chamber;
    determining a second flow measurement value for the flow of fluid flowing through the second measurement chamber, based on the measured electrical potential of the fluid flowing through the second measurement chamber;
    detecting the temperature of the fluid, in the flow sensor, with a temperature sensor integrated in the flow sensor;
    correcting the first flow measurement value and the second flow measurement value, based on the temperature detected in the flow sensor, to form a corrected first flow measurement value and a corrected second flow measurement value; and
    determining a differential flow measurement of the fluid flowing through the first and second measurement chambers by offsetting the corrected first flow measurement value with the corrected second flow measurement value.

11. The method in accordance with claim 10, further comprising the step of:

detecting the conductivity of the fluid by means of a conductivity sensor integrated in the flow sensor.

* * * * *